(12) United States Patent
Patel et al.

(10) Patent No.: US 10,842,511 B2
(45) Date of Patent: Nov. 24, 2020

(54) INSTRUMENTS FOR GUIDING PLACEMENT OF IMPLANTS

(71) Applicant: CUTTING EDGE SPINE LLC, Waxhaw, NC (US)

(72) Inventors: Shyam Patel, Waxhaw, NC (US); Kyle Kuntz, Waxhaw, NC (US)

(73) Assignee: CUTTING EDGE SPINE LLC, Waxhaw, NC (US)

( * ) Notice: Subject to any disclaimer, the term of this patent is extended or adjusted under 35 U.S.C. 154(b) by 17 days.

(21) Appl. No.: 16/121,571

(22) Filed: Sep. 4, 2018

(65) Prior Publication Data
US 2019/0192197 A1 Jun. 27, 2019

Related U.S. Application Data

(60) Provisional application No. 62/554,276, filed on Sep. 5, 2017.

(51) Int. Cl.
*A61B 17/17* (2006.01)
*A61B 17/70* (2006.01)
*A61B 90/00* (2016.01)
*A61B 17/90* (2006.01)
*A61B 17/32* (2006.01)

(52) U.S. Cl.
CPC ...... *A61B 17/1757* (2013.01); *A61B 17/1739* (2013.01); *A61B 17/7055* (2013.01); *A61B 17/7074* (2013.01); *A61B 90/39* (2016.02); *A61B 2017/320052* (2013.01); *A61B 2017/90* (2013.01); *A61B 2090/3966* (2016.02)

(58) Field of Classification Search
CPC . A61B 17/17; A61B 17/1703; A61B 17/1739; A61B 17/1757; A61B 2017/320052; A61B 17/7055; A61B 17/7074; A61B 17/7083; A61B 2017/90; A61B 2090/3966
See application file for complete search history.

(56) References Cited

U.S. PATENT DOCUMENTS

| | | | | |
|---|---|---|---|---|
| 4,383,527 A | * | 5/1983 | Asnis | A61B 17/1721 606/96 |
| 5,415,502 A | * | 5/1995 | Dahlin | B23B 47/28 408/115 B |
| 7,819,879 B2 | * | 10/2010 | Penenberg | A61B 17/175 606/86 R |
| 8,043,297 B2 | * | 10/2011 | Grady, Jr. | A61B 17/1728 606/98 |

(Continued)

*Primary Examiner* — Larry E Waggle, Jr.
(74) *Attorney, Agent, or Firm* — McNees Wallace & Nurick LLC

(57) ABSTRACT

A surgical guide assembly for selecting a target site for insertion of a fixation implant, the surgical guide used in conjunction with fluoroscopy or other x-ray-based imaging for selecting a target site into bone based upon a rendered radiographic image of the bone. The guide includes a planar radiolucent guide tool with radiopaque markers and seats for accommodating securement components that can be engaged in apertures within securement seats of the radiolucent guide tool and contacted or positioned adjacent target bone for establishing a path to a bone target to guide the placement of an implant relative to a reference point, such as a first implant. In the guide tool may include visual indicia corresponding with one or more of the securement seats.

17 Claims, 8 Drawing Sheets

(56) References Cited

U.S. PATENT DOCUMENTS

| | | | | |
|---|---|---|---|---|
| 8,366,711 | B2* | 2/2013 | Rabiner | A61B 17/68 606/63 |
| 9,119,645 | B2* | 9/2015 | McBride | A61B 17/1757 |
| 2003/0236527 | A1* | 12/2003 | Kawakami | A61B 17/1721 606/96 |
| 2017/0007307 | A1* | 1/2017 | Cocaign | A61B 90/06 |
| 2017/0189037 | A1* | 7/2017 | McGinley | A61B 17/1617 |

* cited by examiner

INSTRUMENTS FOR GUIDING PLACEMENT OF IMPLANTS

PRIORITY

This application claims the benefit under 35 U.S.C. § 119(e) to U.S. Provisional Application Ser. No. 62/554,276 filed Sep. 5, 2017, the entirety of which is incorporated herein by reference.

FIELD

The present application describes various exemplary devices and surgical techniques for directing placement of an implant into bone.

DESCRIPTION OF THE RELATED ART

In the context of orthopedics, a variety of conditions, including injuries, degeneration, and congenital abnormalities can present the need for interventional implants and surgical techniques to achieve one or more of bone repair, stabilization, and correction. In one example, fixation and fusion is needed for addressing sacroiliac dysfunction or instability that occurs in the sacroiliac joint. In a typical subject, the sacroiliac joint spans between the sacrum bone and ilium bone, and has a natural degree or motion, or nutation, of one to two degrees. Once diagnosed, there are various surgical options for bone repair, typically involving insertion of one or more implants into bone. Such implants may be threaded or not threaded, and when used in combinations, the combinations may include threaded and non-threaded forms. Particularly when multiple implants are to be used, it is desirable to achieve spacing between the implants that avoids interference between them, while ensuring placement of each implant in bone in a manner that does not result in breach of the implant through a distal portion of the bone and into contact with soft tissue. Problems with placement are typically managed using fluoroscopy. However, challenges remain in terms of achieving optimal placement of multiple implants. Accordingly, there is a need for devices that can improve and enhance the targeting of implant placement for bone fixation.

SUMMARY

In accordance with the various embodiments, provided here is a surgical guide assembly for establishing a path for accessing a target site in bone, in particular for placement of a fixation element into the target site. The assembly may be used for placement of one or more fixation elements or implants, the target positions for each based on a reference point on the bone corresponding to a reference location on the surgical guide assembly. The surgical guide assembly may be used in particular for providing a drill guide path for preparing bone to receive a wire or implant. The guide assembly includes a radiolucent guide tool that includes at least one reference securement seat, and a plurality of target path securement seats. Each of the target path securement seats is arranged at a different fixed distance from the reference securement seat. Each of the reference securement seats and target path securement seats includes an aperture for receiving and seating a securement component, the aperture and the securement components aligned along a securement seat axis that is concentric with a center point of the securement seat and in an antiparallel orientation to the radiolucent guide tool. In various embodiments the surgical guide assembly also includes two or more securement components, each securement component being substantially tubular and engageable with a securement seat on the guide tool. Also provided is a method for use of the surgical guide assembly for placement of an implant into bone.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
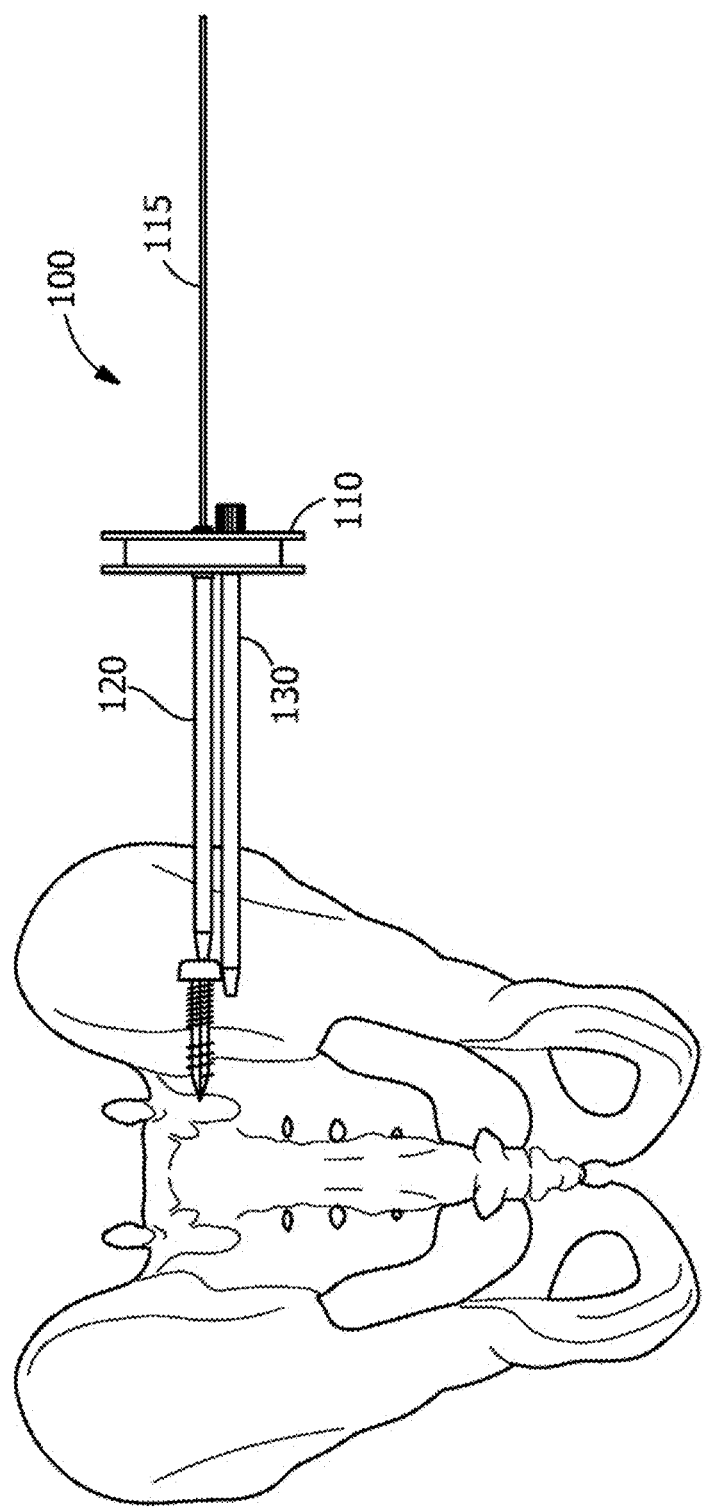
FIG. 1 shows an anterior to posterior view depiction of the pelvic bones with the guide assembly 100 shown in side view and engaged at a lateral surface relative to the sacroiliac joint, and engaged through a central guide body with a K-wire.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

The general inventive concepts will now be described with occasional reference to the exemplary embodiments of the invention. The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community, and generally, any and all terms providing spatial references to anatomical features shall have meaning that is customary in the art. For example, the application may include reference to the following terms: "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the mid line of the patient, and away from the side, the term "ipsalateral" indicates a direction toward a side that is proximal to the operator or the object being referenced, and the term "contralateral" indicates a direction toward a side that is distal to the operator or the object being referenced.

"Patient" is used to describe an animal, preferably a human, to whom treatment is administered, including prophylactic treatment with the compositions of the present invention.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, some references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

Provided are tools and methods for facilitating tissue fixation, such as but not limited to, sacroiliac joint fixation to facilitate fusion thereof. It will be appreciated that the examples and drawings, as shown herein, may be described in reference to use in applications for sacroiliac joint fusion, though the devices as disclosed herein may be used in any of a variety of other orthopedic applications, and may be used alone, or as an adjunct to devices used for other fixation or correction, such as, for example, in spine fusion surgery, to help guidether orthopedic implants into placement within bone.

The tools include a surgical guide assembly 100 instrument adapted for placing at least two fixation implants, which may be selected from any of a variety of known fixation implants that may be threaded or unthreaded and may be cannulated or not-cannulated. In some embodiments, the guide assembly is used as a drill guide for establishing the path for placement of a fixation implant and including a guide tube or the like for directing a drill bit or other tool passed therethrough and into contact with the target bone site.

The methods include techniques for use of the drill guide and, in some embodiments, are generally characterized as including the steps of placing a guide wire (or a Kirchner wire, or K-wire) at an insertion site for the implant, inserting a fixation member over the wire, inserting a cannulated drill guide over the guide wire and using a cannulated drill to pre-drill a pilot hole, and then inserting the screw onto the guide wire to direct the path for insertion into the bone, then using a cannulated driver or other appropriate tool to drive the implant into the bone to traverse the joint and thereby join the sacrum and the ilium, then selecting the desired placement option for a second implant and following the previous steps for the second implant. It will be appreciated that in some embodiments, one or more of the fixation members may not be cannulated, thus the steps of implantation may vary accordingly.

Guide Instruments for Implant Placement

Figure 2:
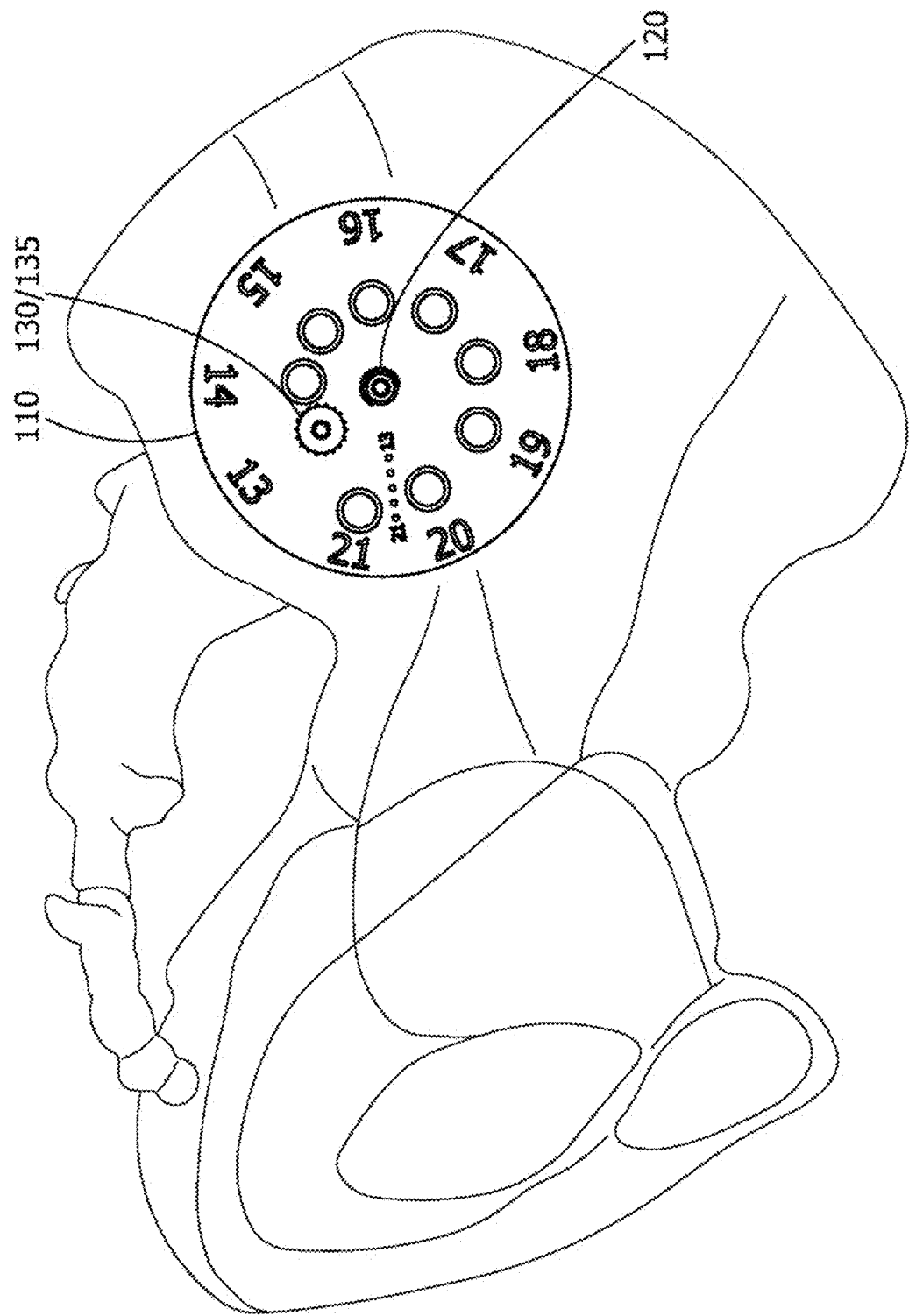
FIG. 2 shows a top plan view of the guide assembly 100 radiolucent guide tool 110 in association with a pelvic bone from a lateral aspect.
Figure 3:
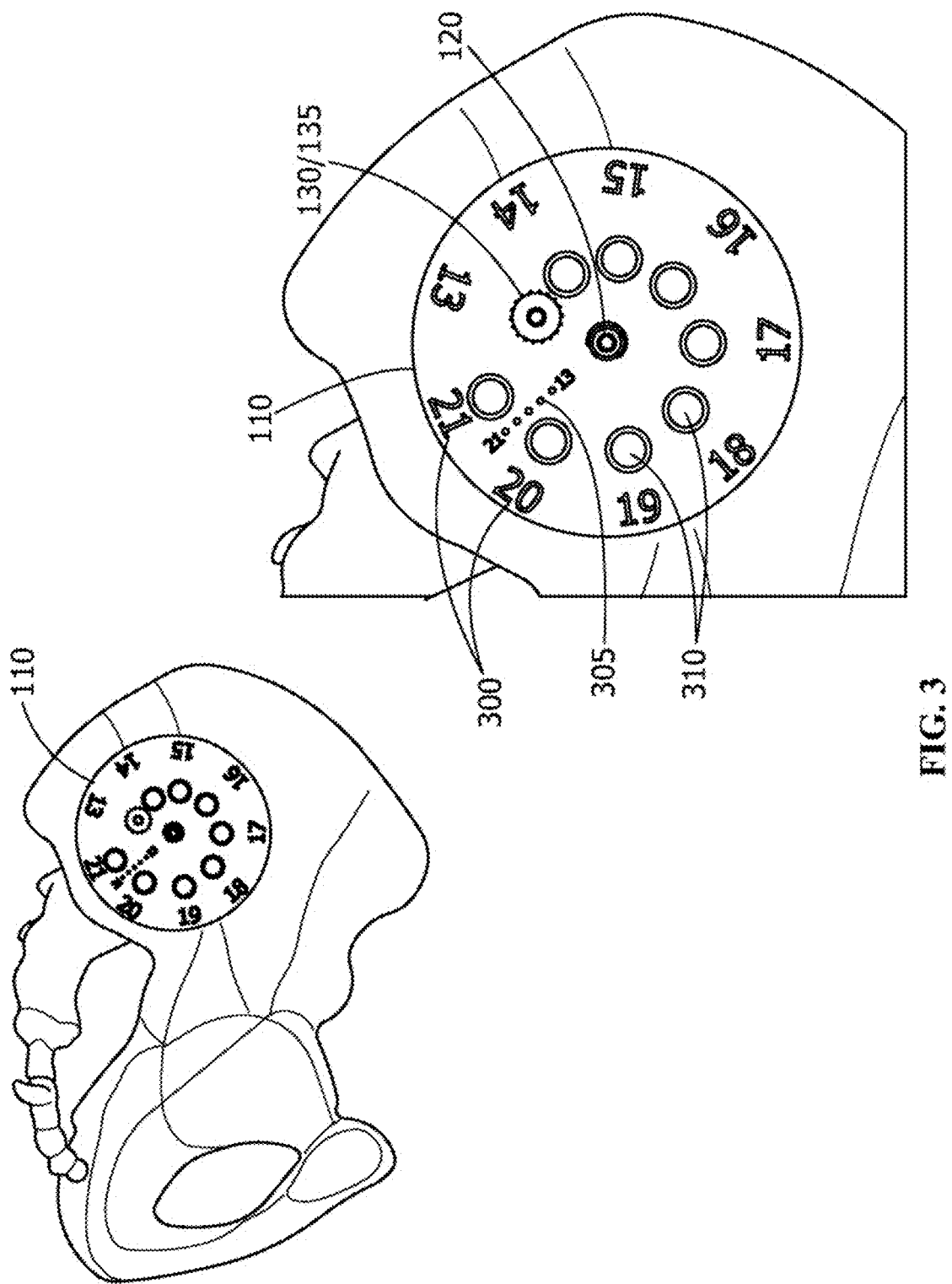
FIG. 3 shows a top plan view of the guide assembly 100 radiolucent guide tool 110 in association with a pelvic bone from a lateral aspect and a close-up view of the same.

In a representative embodiment, as depicted in each of FIG. 1-FIG. 3 the guide assembly 100 is used in selecting a target site for insertion of a fixation implant, in conjunction with fluoroscopy or other x-ray-based imaging. The selection of the target site on the bone is based upon a rendered radiographic image of the bone. The guide assembly 100 as depicted includes: (i) a radiolucent guide tool 110 comprising a reference securement seat 220 that comprises an aperture for receiving a reference tube 120 (via a tube aperture 310), the reference securement seat 220 in some embodiments further comprising a locking feature 125. The radiolucent tool guide 110 further includes a plurality of two or more guide assembly 100 target path securement seats 230 each comprising an aperture 310 for receiving a guide tube 130 (via a tube aperture 310), each of the target path securement seats 230 in the plurality arranged at increasing graduated distances relative to the reference securement seat 220, an array of radiopaque markers 305 and corresponding visual indicia 300 (visual and/or tactile indicators) oriented adjacent to each of the two or more guide assembly 100 target path securement seats 230 and optionally the reference securement seat 220 (tube aperture 310), the visual indicia indicating the distance of each of the target path securement seats 230 from the reference securement seat 220. Each of the target path securement seats 230 (tube aperture 310) is adapted to receive an elongate securement component (guide tube 130) that is engageable with target path securement seats 230 (via the tube aperture 310) along an axis that is parallel with a center point (reference securement seat tube aperture 220/310) of the reference securement seat 220 and in an antiparallel orientation to the radiolucent guide tool 110. As shown, the radiolucent guide tool 110 is planar and generally disc or cylindrically shaped. In other embodiments, the shape may be more tubular, or may have a shape that is other than circular, for instance the shape may be square.

The radiopaque 305 markers comprise any radiopaque 305 material selected from solid beads, wire, paint, and combinations of these, and wherein the visual indicia are selected from numbers, letters, symbols and combinations of these that are one of painted, etched, labeled, printed, and embossed on the radiolucent guide tool. The guide assembly 100 also includes two or more elongate securement components (reference tube 120, guide tube 130), each elongate securement component tube 120, 130 being substantially tubular and comprising a proximal engagement feature 135 that is releasably engageable with the corresponding securement seat 120, 130 locking feature complimentary securement feature 235. Referring again to FIG. 1, an elongate securement component (reference tube 120), when fixed to the radiolucent guide tool 110 at the reference securement seat 220 (via a tube aperture 310), is engageable with a guide wire 115 placed at a selected reference location in a bone, thereby fixing a reference point on the radiolucent guide tool 110. Under fluoroscopy, the radiolucent guide tool 110 is rotatable to enable selection of a desired bone target by orientation of the radiopaque 305 indicia over the target site. Insertion and engagement of an elongate securement component (guide tube 130) into the selected drill guide target path securement seats 230 (tube aperture 310) corresponding to the bone target, establishes the insertion site for a fixation implant into the bone.

Referring now to FIG. 1, an exemplary embodiment of a fixation member guide assembly 100 is shown in association with bony anatomy. The guide assembly 100 is used to guide a second guide wire generally parallel to and spaced a specific distance from a first guide wire already placed in bone so as to precisely establish the desired positioning of two implants. Of course, the assembly may be used by sequential steps to place additional implants or select the options for placing additional implants. The position of the second wire can vary in specific distance increments from the first wire according to a predetermined spacing that is governed by the placement of target path securement seats 230, and markers/indicators 300 associated with discrete guide tube apertures 310 in the radiolucent guide tool 110 of the guide assembly 100.

Figure 4:
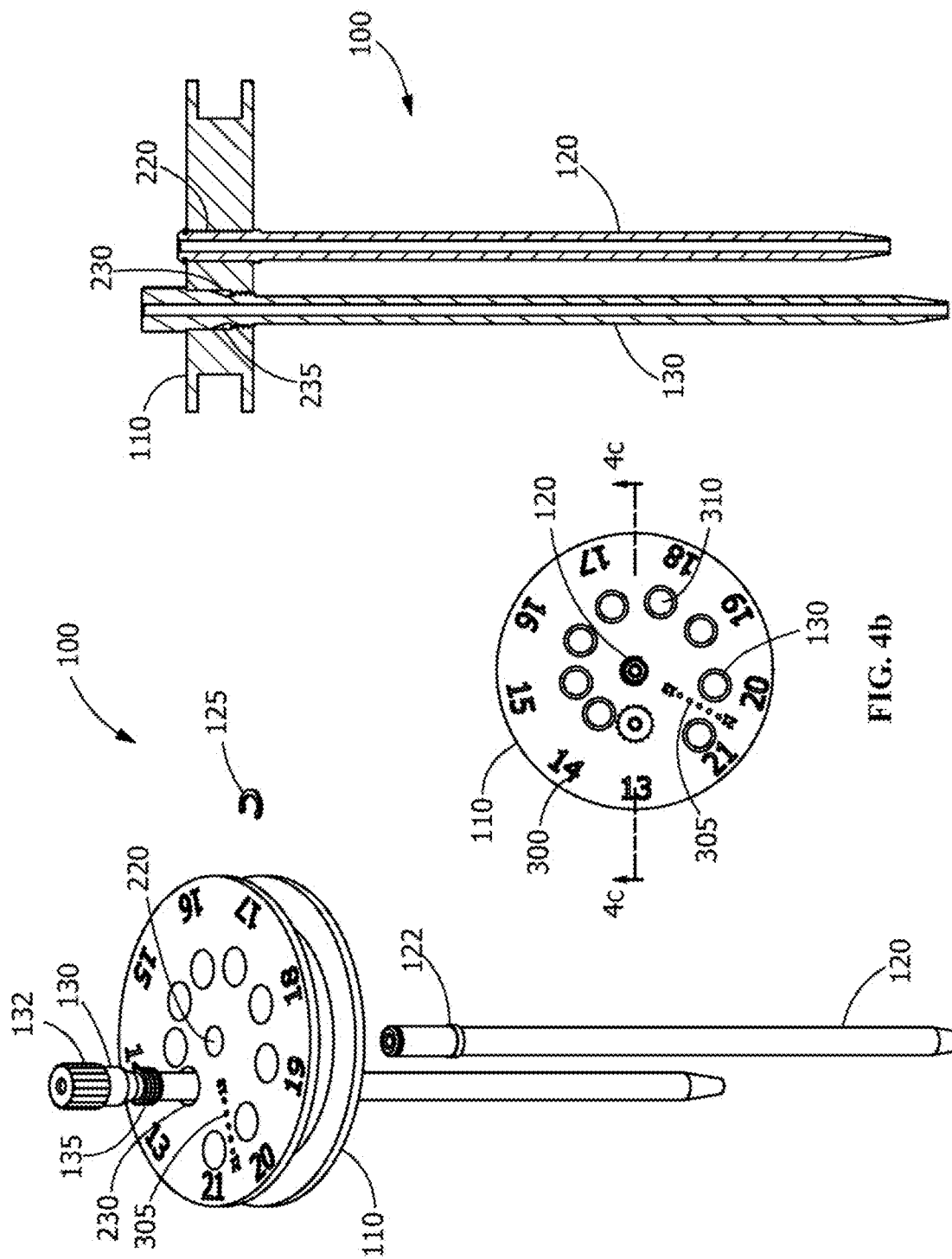
FIG. 4a shows an isometric exploded view of a surgical guide assembly 100 for placement of at least two fixation implant members according to the disclosure.
FIG. 4b shows an alternate view of a surgical guide assembly 100, namely a top plan view of the guide assembly 100 radiolucent guide tool 110.
FIG. 4c shows another view of a surgical guide assembly 100, namely a side cross sectional side view of the drill guide assembly.
Figure 5:
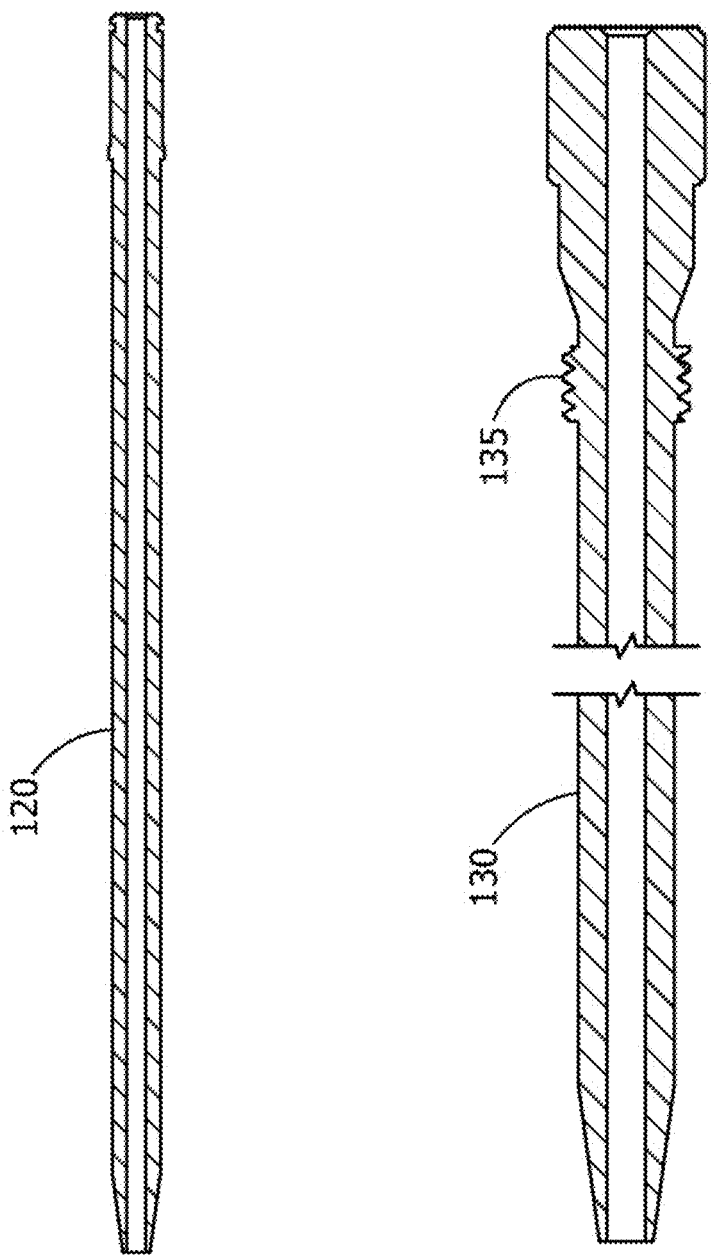
FIG. 5 shows cross sectional views transverse to and parallel to the axis of each of two guide tube components 120, 130 of a surgical guide assembly 100 according to the disclosure.

Referring now to FIG. 3 and FIG. 4, in accordance with the various embodiments, the components of the guide assembly 100 include a radiolucent guide tool 110, at least first and second guide tubes 120 and 130, each adapted to engage with the radiolucent guide tool 110 via apertures 310 for establishing the relative positioning and placement of guide wires for implant components. Each component of the guide assembly 100, in some embodiments, is formed with a material that is radiolucent, thus, in such embodiments, each of the radiolucent guide tool 110, and tubes 120, 130 is formed of a radiolucent material. In some embodiments, at least the guide tube 130 is formed entirely suitable for receiving a drill. In some embodiments, one or more of the reference tube 120 and guide tubes 130 may be formed at least partially with a radiopaque 305 material to facilitate their relative alignment with the radiolucent guide tool 110 and/or bone. In some embodiments, one or more of the reference tube 120 and guide tubes 130 may include radiopaque 305 materials, such as tantalum wire, beads, or paint.

The radiolucent guide tool 110 includes one or more of visual and/or tactile indicators 300 which designate the distance from a reference point on the radiolucent guide tool 110, for example from an aperture 310 to the center of the radiolucent guide tool 110 which is adapted to receive a reference tube 120, the distance predetermined from the guide tube aperture 220 to each of a plurality of guide tube apertures 310 in the radiolucent guide tool 110, the apertures 310 adapted for receiving a guide tube 130. Each of the components is sized for interengagement, the reference tube 120 being sized for engagement with at least the guide tube aperture 220, and the guide tube 130 being likewise sized and shaped for engagement with one of the target path securement seats 230.

The radiolucent guide tool 110 further includes radiopaque 305 markers embedded in or affixed to the radiolucent guide tool 110, the radiopaque 305 markers affixed and corresponding with the visual and/or tactile indicators 300. In use, the radiopaque 305 markers are visualized with fluoroscopy so as to align with bone and enable selection of desired locus for implant placement relative to a reference point established using the radiolucent guide tool 110 and/or, which reference point is either the reference securement seat 220 reference tube aperture 310 or a preplaced implant or guide wire inserted in the bone and in communication through one of the apertures 310 of the radiolucent guide tool 110. The radiopaque 305 markers may be formed using any one or more of known radiopaque 305 materials, including, for example, tantalum containing beads, rods, wires, paint and the like. In one example, the radiopaque 305 markers are tantalum beads embedded in the radiolucent guide tool 110 adjacent to a visual indicator 300. In another example, the radiopaque 305 markers are tantalum wires that are associated with the visual and/or tactile indicators 300. In yet other examples, the radiopaque 305 markers are formed at least in part with opaque paint that is applied to or near one or more of the visual and/or tactile indicators 300.

In various embodiments, the radiolucent guide tool 110 is sized and the positioning of the reference securement seat 220 reference tube aperture 310 and target path securement seat 230 reference tube apertures 310 are predetermined for use with correspondingly sized implants to optimize placement and avoid interference of implants. Referring again to the drawings, for example FIG. 2, guide assembly 100 components are shown with representative markings on the radiolucent guide tool 110 and in some embodiments, the tube 120, 130 components, wherein the markings reflect distances in increments of millimeters relative to the center point of the radiolucent guide tool 110 which includes the reference securement seat 220 reference tube aperture 310.

Thus, in various embodiments, the spacing of target path securement seat 230 reference tube apertures 310 is predetermined and the apertures may be separated in any desired increments, such as for example in mm or fractions thereof. And there may be more or fewer target path securement seat 230 reference tube apertures 310 than are shown in the drawings. Each of the apertures 310, generally, may be the same diameter or the reference securement seat 220 reference tube aperture 310 may be different in its circumferential and other dimensions from the target path securement seats 230. Thus, the reference and the guide tubes 120, 130, generally, may be the same diameter as the aperture 310 through which it is passed, or the reference tube 120 may, for example, have different internal and external diameter dimensions as compared with those of the guide tube 130, and thus the plurality of apertures 310 may have different diameters. It will be generally understood that the apertures 310 are sized for receiving the intended tubes, thus the reference securement seat 220 reference tube aperture 310 is sized to receive the reference tube 120, and the target path securement seat 230 reference tube apertures 310 are sized for receiving the guide tubes 130. Likewise, the reference tube 120 and guide tubes 130 are sized for receiving standard surgical wires or K-wires, and the apertures 310 are thus sized accordingly. In some examples, one or more of the reference tube 120 and guide tubes 130 are configured in shape and formed of materials suitable for passage of a drill bit or similar tool through their centers for contacting bone.

It will be appreciated that in other embodiments, the apertures 310 may be sized for receiving in addition to or as an alternative to the reference tubes 120 and guide tubes 130, including other tools, instruments, implants and fasteners, the placement of which relative to bone is facilitated by use of the radiopaque indicators 305 of the radiolucent guide tool 110. In various embodiments, an assembly 100 may include a selection of tubes 120, 130, each with the selection having varying internal diameters corresponding to different wire diameters and different features of tools to be passed therethrough, and likewise, a selection of radiolucent guide tools 110 may be provided, each having aperture 310 sizing and spacing that varies to accommodate different surgical wire diameters, and/or for passage of other tools and instruments, and/or for placement of implants of different sizes.

Referring again to FIG. 4, a cross sectional view of the guide assembly 100 shows engagement with the radiolucent guide tool 110 of each of a reference tube 120 through a guide tube aperture 220 and a guide tube 130 through a target path securement seat 230 tube aperture 310. As shown, the guide tube 130 is adapted with an engagement feature 135, which as shown is male threading, the engagement feature 135 of the guide tube 130 adapted to interengage with a complementary securement feature 235 within the target path securement seat 230 tube aperture 310 (the securement feature shown as corresponding threads). As shown, the guide tube 130 is adapted with a knurled knob 132 that facilitates control and engagement with the radiolucent guide tool 110. It will be appreciated that other engagement means may be selected for securing the guide tube 130 within the target path securement seat 230 tube aperture 310 of the radiolucent guide tool 110, including but not limited to luer and/or Morse type male and complimentary female tapers.

As shown in FIG. 4a, in some embodiments at least the guide tube aperture 220 is adapted for receiving and engaging with a reference tube 120 via a securement element. As shown, the reference tube 120 is adapted with an engagement feature 122, which includes a circumferential feature that is adapted to engage with a complementary securement feature 125 within the guide tube aperture 220 (the securement feature shown as a clip or washer that is compressed within the aperture). It will be appreciated that other engagement means may be selected for securing the reference tube 120 within the guide tube aperture 220 of the radiolucent guide tool 110.

In use, as described herein below, a guide wire that is pre-inserted into bone is passed through the reference tube 120, the radiolucent guide tool 110 is engaged with the reference tube 120. Under fluoroscopy, the radiolucent guide tool 110 is rotated to align one of the radiopaque 305 markers with the surgeon's selected target on the bone. The user thereafter passes a guide tube 130 through the target path securement seat 230 tube aperture 310 corresponding with the selected reference marker and secures the guide tube to the radiolucent guide tool 110. It will be appreciated that the guide assembly 100 provides more accurate and controlled placement options for a second implant relative to an initial implant target. Moreover, the radiolucent guide tool 110 spacing when predetermined based on specific implant sizing, ensures that selection of any position from the array of target path securement seats 230 guide tube apertures 310 will allow avoidance of implant interference in the bone.

It will be appreciated that the description herein and the embodiments as shown in the figures are merely representative, and the guide assembly 100 may be used in any tissue of the body, particularly bone tissue, and may be used with surgical wires or any other suitable material to facilitate controlled and oriented placement of implants within tissue. Thus, the description of surgical technique, below, and the examples described herein above and shown in the drawings are not limiting with respect to the tissue, the type of implant or the number of implants:

Example 1: Surgical Technique with Linear Radiopaque Marker Array

With reference again to the exemplified assembly 100 as shown in FIG. 1, the surgical technique outlined below is followed for use of the guide assembly 100 in connection with placement of a guide wire into a sacral iliac joint to facilitate placement of a screw type implant, as depicted. Of course, the guide assembly 100 can be used in a similar manner for any number of other clinical applications that are not limited to implant placement in a sacral iliac joint.

The reference tube 120 of the guide assembly 100 is passed over a pre-secured K-wire that extends from the bone at its distal end to a location that is proximal to the surgeon. Care is taken to carefully align the plane of the radiolucent guide tool 110 relative to a plane corresponding to the bone surface under fluoroscopy. According to this example, an array of radiopaque markers 305 (shown in the drawings as a linear array of beads) is positioned on the radiolucent guide tool 110 and discrete radiopaque markers within the array 305 are oriented and spaced apart from one another in a manner wherein each bead is positioned at a predetermined distance from the reference securement seat 220 and corresponding to the radial position of a target path securement seat 230 tube aperture 310. Thus, according to the embodiment as shown in the drawings, the array 305 includes beads at distances that are, respectively, 13, 15, 17, 19 and 21 mm from the center point of the reference securement seat 220 reference tube aperture 310, wherein the half way point between any two adjacent beads corresponds, respectively, to distances of 14, 16, 18 and 20 mm. It will be appreciated that more or fewer radiopaque markers, in the form of beads or otherwise, may be used relative to the number of target path securement seat 230 reference tube apertures 310 used for seating a guide tube 130. Thus, in some examples there may be a discrete radiopaque marker for each target path securement seat 230, and in other embodiments there may be fewer. Further, the radiopaque markers may be arranged other than in a linear array. It will be appreciated that embodiments thereof are not limited to a mm scale with respect to distances between apertures 310, radiopaque indicia and the like.

Figure 6:
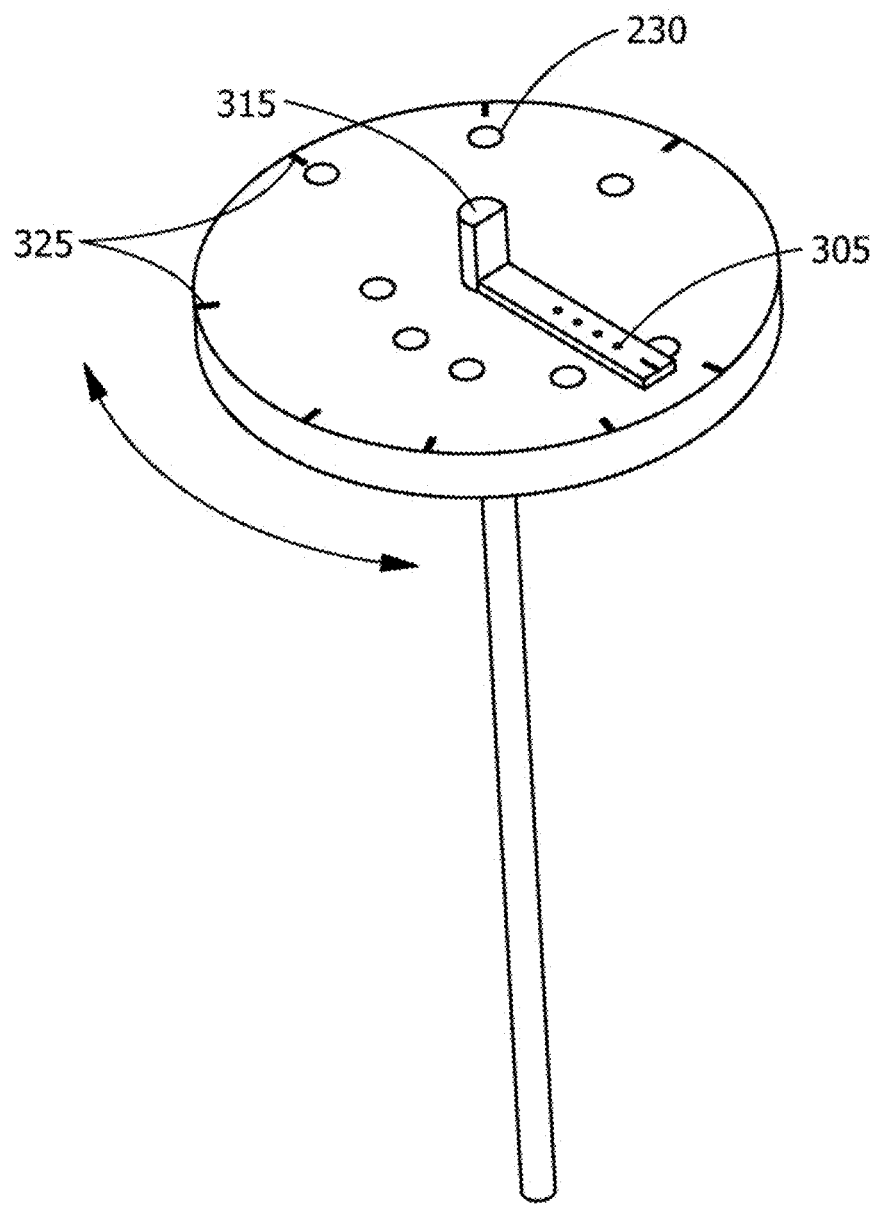
FIG. 6 shows an alternate embodiment of a drill guide assembly according to the disclosure.

In one alternate embodiment, the linear array may be arranged on a secondary disc, guide arm, or other component that is removably engageable with the guide assembly 100 and adapted for using the same axis as the reference guide aperture. Referring now to FIG. 6, an arm 315 is shown that bears radiopaque markers 305 in a linear array wherein the arm 315 is movable separately from the radiolucent guide tool 110. Using orientation markers, such as the radially positioned markers 325 around the periphery of the radiolucent guide tool 110, the arm 315 may be rotated into position over the target bone under fluoroscopy, and the desired location on the bone oriented with a radiopaque indicator in the array, then the radiolucent guide tool 110 may be rotated in a manner to orient the corresponding target path securement seat 230 reference tube aperture 310 with the selected discrete position along the radiopaque marker 305 on the arm 315. The arm 315 can be removed from the guide assembly 100 to enable access to the selected target path securement seat 230 reference tube aperture 310 for direct placement of the guide wire 115 towards the target.

Steps according to the method include: Place the short tube in center of radiolucent guide tool 110 over the existing K-wire. Rotate the array of markers above the marked sacral alar line on the skin or another trajectory of sacrum as desired by surgeon.

Figure 7:
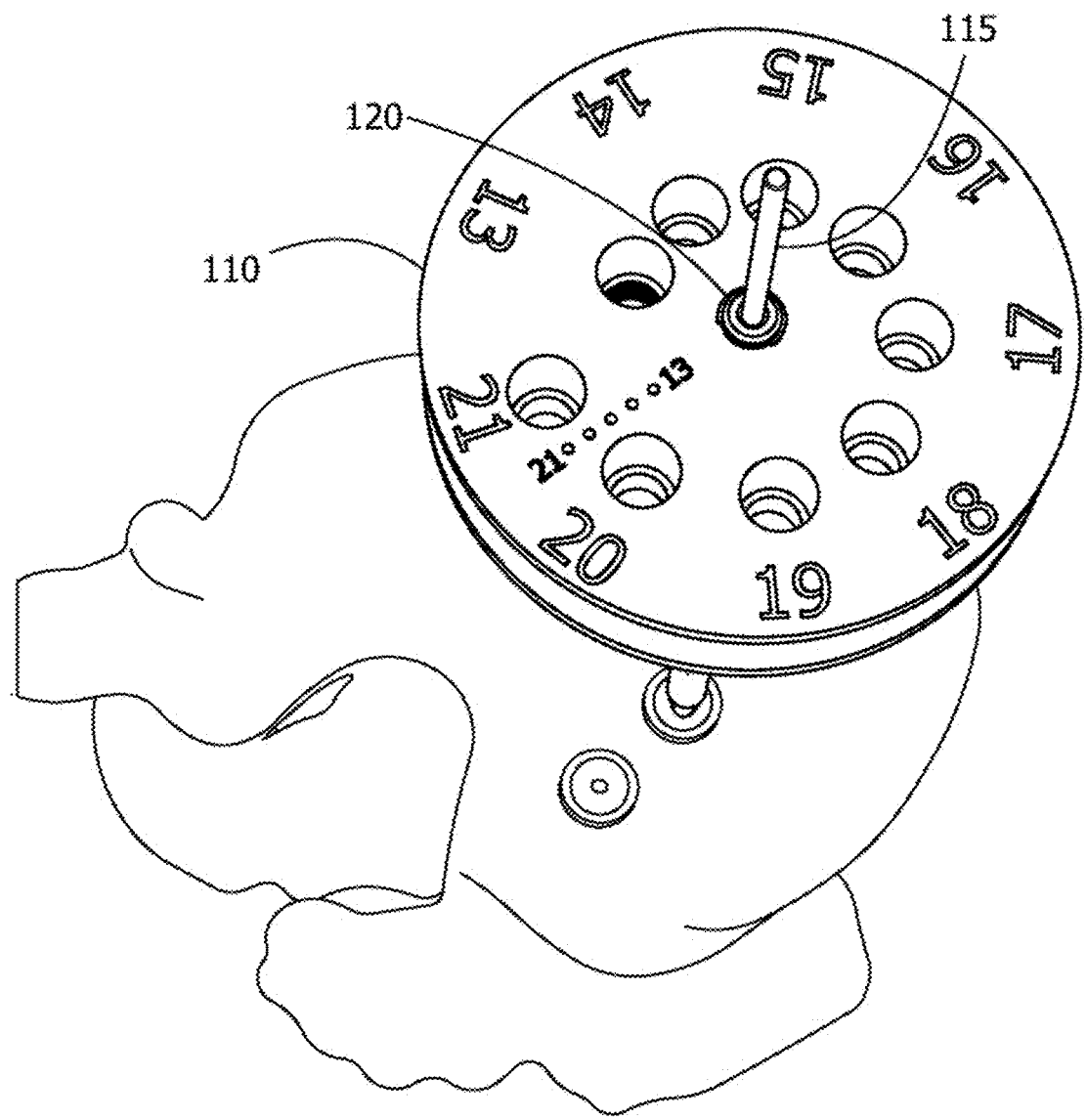
FIG. 7 shows a different top plan view of the guide assembly 100 radiolucent guide tool 110 in association with a pelvic bone from a lateral aspect; and, FIG. 8 shows a different top plan view of the guide assembly 100 radiolucent guide tool 110 in association with a pelvic bone from a lateral aspect.

To determine the placement of the second wire, use appropriate medical imaging while making sure the lateral image is directly along the axis of the first K-wire. Shot under radiography from a lateral view (see FIG. 7).

Determine the spacing needed from the linear array of the radiopaque markers by selecting the marker itself or the space in between markers.

Figure 8:
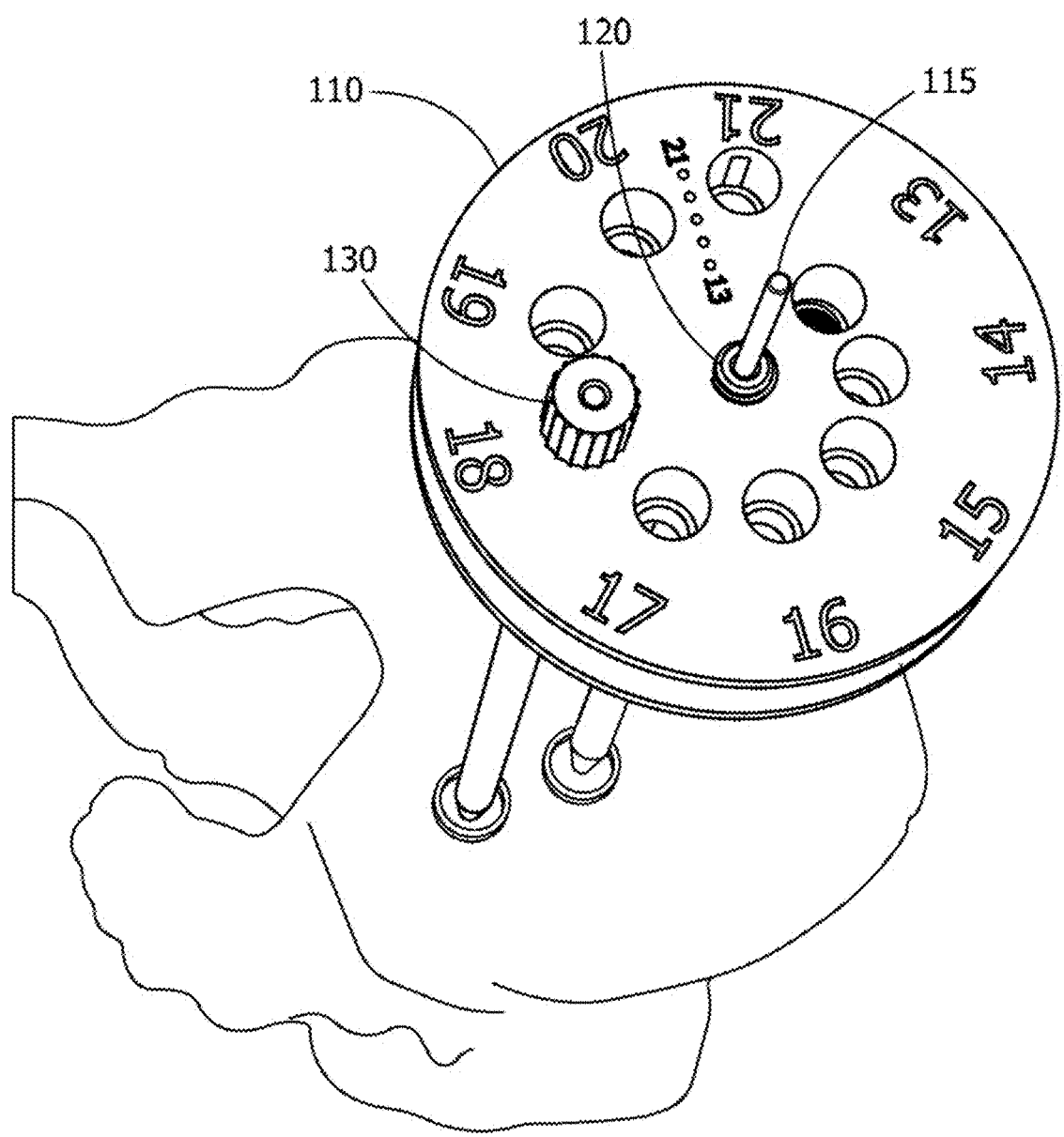

Rotate the radiolucent guide tool 110 to the determined spacing and line up the diameter of the hole to the selected trajectory in step 1 to provide the closest approximation for accuracy without another medical imaging shot. Thread in the second wire guide to selected spacing and add second K-wire through cannulation of second wire guide (see FIG. 8). Shot is not necessary to be under radiography. Radiography can be used to make finite adjustments radially.

Advancing the K-wire may require fluoroscopy shots in inlet and outlet views but this would be the next step after using this instrument.

In yet another embodiment, the linear array of radiopaque markers may be on a secondary disc, arm or plate that can rotate radially using the same axis as the reference guide aperture. It would be placed on top of the radiolucent guide tool 110, each rotatable independently. Using fluoroscopy, determine the spacing needed (same as step 2-3). After determining the space needed, the secondary plate is held in place and the radiolucent guide tool 110 is rotated such that the correspondingly positioned aperture aligns with the selected radiopaque bead. In some embodiments, features on one of the reference tube 120 and the radiolucent guide tool 110 can facilitate fixation of the secondary disc in place while the radiolucent guide tool 110 is rotated. Once the selected target path securement seat 230 reference tube aperture 310 is lined up with secondary plate using radially positioned markers 325 (see FIG. 6) and the exact position is fixed, the secondary plate can be removed. Then thread the second wire guide and place the second K-wire through the cannulation of the second wire guide. Fluoroscopy is not necessary again but can be used to make finite radial adjustments if the radiolucent guide tool 110 might have moved Example 2: Surgical Technique with Radially Positioned and Movable Radiopaque Markers Again, with reference to the example as shown in FIG. 1, the following steps are followed for an alternate use of the drill guide assembly in connection with placement of a guide wire into a sacral iliac joint to facilitate placement of a screw type implant, as depicted. The reference tube 120 of the guide assembly 100 is passed over a pre-secured K-wire that extends from the bone at its distal end to a location that is proximal to the surgeon. Care is taken to carefully align the plane of the radiolucent guide tool 110 relative to a plane corresponding to the bone surface under fluoroscopy.

The radiopaque markers are, in one embodiment, co-located with visual indicators 300 (shown in the drawings by way of example as numeral markings that are adjacent with the apertures positioned at mm increments from 13 mm to 21 mm from the center of the reference securement seat 220 reference tube aperture 310 can be used to determine implant spacing. A lateral radiographic image is taken to confirm that the assembly is aligned along the axis of the first K-wire to avoid distortion and inaccurate placement of the additional implant. According to one embodiment, the radiopaque markers are positioned adjacent the visual indicators 300 or the apertures. In some specific embodiments, the radiopaque markers define the periphery of each aperture. In a particular embodiment, the radiopaque markers are arranged on a secondary disc that is removably engagable with the assembly 100. In use, the secondary disc is placed over the radiolucent guide tool 110 and each of the discrete radiopaque markers positioned thereon can be aligned with the center point of its corresponding target path securement seat 230. Under fluoroscopy, the bone target can be aligned with a radiopaque marker, then the secondary disc can be removed to enable access to the selected target path securement seat 230 reference tube aperture 310 for direct placement of the guide wire 115 towards the target.

Using the drill guide, the appropriate spacing is determined by the surgeon by rotating the radiolucent guide tool 110 such that the selected marker is aligned over the bone, thus orienting the corresponding aperture over the bone. The guide tube 130 is passed through the selected aperture and is secured to the radiolucent guide tool 110.

A K-wire is passed through the secured guide tube 130 and directed across the sacroiliac joint and into the sacrum using frequent fluoroscopic imaging in lateral, anterior to posterior and superior to inferior views, as deemed appropriate by the surgeon. The assembly is removed upon placement of the guide wire.

The procedure may be repeated for placement of supplemental wires that may be used to guide the path for placement of additional screws or other implants.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A surgical guide assembly for establishing an insertion path for a fixation implant, the guide assembly comprising:
    (i) a radiolucent guide tool comprising:
        a reference securement seat;
        a plurality of target path securement seats; and
        an array of radiopaque markers,
        each of the target path securement seats being arranged at different fixed distances from the reference securement seat,
        each of the reference securement seat and target path securement seats comprising an aperture, and
        the radiopaque markers in the array being arranged to correspond with the fixed distances of the guide assembly target path securement seats from the reference securement seat; and
    (ii) a first securement component that is substantially tubular and is insertable into a selected reference securement seat to establish a first path for passage of a first tool,
    wherein either (a) the radiolucent guide tool is movable with respect to an inserted securement component, or (b) the radiolucent guide tool further comprises a movable part that comprises the array of radiopaque markers and is separately movable relative to the radiolucent guide tool to enable selection of a target path securement seat relative to a selected bone target by orientation of at least one radiopaque marker over the bone target, and
    wherein the radiolucent guide tool further comprises a movable arm that comprises the array of radiopaque markers, wherein the array of radiopaque markers is separately movable relative to the radiolucent guide tool to effect selection of a bone target.

2. The surgical guide assembly according to claim 1, comprising a plurality of corresponding visual indicia oriented adjacent to each of the target path securement seats.

3. The surgical guide assembly according to claim 2, wherein the plurality of corresponding visual indicia oriented adjacent to each of the target path securement seats comprises a feature indicating a distance of each of the securement seats from the reference securement seat.

4. The surgical guide assembly according to claim 2, wherein the visual indicia are selected from numbers, letters, symbols and combinations of these, and wherein the visual indicia are one or more of painted, etched, labeled, printed, and embossed on the radiolucent guide tool.

5. The surgical guide assembly according to claim 1, wherein the radiolucent guide tool is generally planar and has a circular configuration, the reference securement seat is in a central region, and the plurality of target path securement seats are arranged radially from the central region.

6. The surgical guide assembly according to claim 1, wherein, each of the securement seats comprises a securement seat locking feature and is adapted to receive a securement component that is engageable with a securement seat along a securement seat axis that is concentric with a center point of the securement seat and in an antiparallel orientation to the radiolucent guide tool.

7. The surgical guide assembly according to claim 6, further comprising at least one additional securement component that is substantially tubular and is insertable into at least one selected target path securement seat to establish an at least one additional path for passage of at least one additional tool, wherein at least one of the first securement component and the at least one additional securement component comprises a proximal locking feature.

8. The surgical guide assembly according to claim 7, wherein the proximal locking feature is releasably engageable with the securement seat locking feature.

9. The surgical guide assembly according to claim 8, wherein the proximal locking feature and the securement seat locking feature each comprises complimentary features selected from threading, and complementary male and female tapers.

10. The surgical guide assembly according to claim 7, wherein the first securement component, when fixed to the radiolucent guide tool at the reference securement seat, is engageable with a guide wire placed at a selected reference location in a bone, thereby fixing a reference point on the radiolucent guide tool relative to the bone.

11. The surgical guide assembly according to claim 1, wherein the array of radiopaque markers comprises any radiopaque material selected from solid beads, wire, paint, and combinations of these.

12. A surgical guide assembly for establishing an insertion path for a fixation implant, the guide assembly comprising:
    (i) a radiolucent guide tool having a shape that is discoid and having first and second sides, each of which sides is, independently, one of planar, convex or domed, and having a circumferential edge, the guide tool comprising:
        a reference securement seat;
        a plurality of target path securement seats; and
        an array of radiopaque markers,
        each of the guide assembly target path securement seats being arranged at different fixed distances from the reference securement seat,
        each of the reference securement seat and target path securement seats comprising an aperture, and
        the radiopaque markers in the array being arranged to correspond with the fixed distances of the guide assembly target path securement seats from the reference securement seat; and
    (ii) two or more securement components, each securement component being substantially tubular and optionally comprising a proximal locking feature, each of the securement components being insertable into a selected reference securement seat or target path securement seat to establish a path for passage of a tool, wherein either (a) the radiolucent guide tool is movable with respect to an inserted securement component, or (b) the radiolucent guide tool further comprises a movable part that comprises the array of radiopaque markers and is separately movable relative to the radiolucent guide tool to enable selection of a target path securement seat relative to a selected bone target by orientation of at least one radiopaque marker over the bone target.

13. The surgical guide assembly according to claim 12, wherein the plurality of target path securement seats are arranged along a line that extends from the reference securement seat.

14. The surgical guide assembly according to claim 12, wherein the radiolucent guide tool comprises the movable part that comprises the array of radiopaque markers, the part being separately movable relative to the radiolucent guide tool.

15. A method for placement of a fixation implant in bone, comprising the steps of:
(a) selecting a surgical guide assembly comprising:
  (i) a radiolucent guide tool having a shape that is discoid or generally cylindrical and having first and second sides, each of which sides is, independently, one of planar, convex or domed, and having a circumferential edge, the guide tool comprising:
    a reference securement seat at a central region of the radiolucent guide tool;
    a plurality of target path securement seats arrayed radially in one of a linear and a spiral configuration relative to the central region; and
    an array of radiopaque markers,
    each of the target path securement seats being arranged at different fixed distances from the reference securement seat,
    each of the reference securement seat and the target path securement seats comprising an aperture,
    the radiopaque markers in the array being arranged relative to the central region to correspond with the fixed distances of the target path securement seats, and
    each of the securement seats being adapted to receive a securement component that is engageable with a securement seat along an axis that is concentric with a center point of the securement seat and in an antiparallel orientation to the radiolucent guide tool; and,
  (ii) two or more securement components, each securement component being substantially tubular, each of the securement components being insertable into a selected reference securement seat or target path securement seat to establish a path for passage of a tool; and
(b) fixing a securement component to the radiolucent guide tool at the reference securement seat, passing the securement component over a guide wire placed at a selected reference location in a bone, thereby fixing a reference point on the radiolucent guide tool relative to the bone, and aligning the array of radiopaque markers into alignment over a target site in bone for receiving an implant, selecting a radiopaque marker corresponding to the target site, and fixing a securement component into a target path securement seat corresponding to the selected radiopaque marker to thereby establish a target path for insertion of a fixation implant in the target site in the bone.

16. The method for placement of a fixation implant in bone according to claim 15, wherein the radiolucent guide tool comprises a movable part that comprises the array of radiopaque markers, the part being separately movable relative to the radiolucent guide tool.

17. A surgical guide assembly for selecting a target site for insertion of a fixation implant into bone, the guide assembly comprising:
(a) a radiolucent guide tool having a generally discoid shape with first and second sides and a circumferential edge, the guide tool comprising a center reference securement seat, a plurality of target path securement seats arrayed radially in one of a linear and a spiral configuration relative to the center reference securement seat and at different fixed distances from the center reference securement seat, each of the center reference securement seat and the target path securement seats comprising an aperture through the radiolucent guide tool, and an array of radiopaque markers positioned on one of the first and second sides and arranged to correspond with the fixed distances of the target path securement seats relative to the center reference securement seat, and
(b) at least one substantially tubular securement component that is affixable by insertion into the aperture of one or more of the center reference securement seat and target path securement seats of the radiolucent guide tool along an axis that is concentric with a center point of the securement seat,
wherein the array of radiopaque markers is separately movable relative to one of the radiolucent guide tool and an inserted securement component to enable selection of a target path securement seat relative to a selected bone target by orientation of at least one radiopaque marker over the bone target.

* * * * *